United States Patent
Pratt et al.

(10) Patent No.: US 6,675,120 B2
(45) Date of Patent: Jan. 6, 2004

(54) COLOR OPTICAL INSPECTION SYSTEM

(75) Inventors: William K. Pratt, Los Altos, CA (US); Owen Y. Sit, Mission Viejo, CA (US)

(73) Assignee: Photon Dynamics, Inc., San Jose, CA (US)

( * ) Notice: Subject to any disclaimer, the term of this patent is extended or adjusted under 35 U.S.C. 154(b) by 228 days.

(21) Appl. No.: 09/892,200

(22) Filed: Jun. 25, 2001

(65) Prior Publication Data

US 2002/0029125 A1 Mar. 7, 2002

Related U.S. Application Data

(60) Provisional application No. 60/214,466, filed on Jun. 27, 2000.

(51) Int. Cl.$^7$ .............................................. G06M 11/04
(52) U.S. Cl. ........................................ 702/127; 382/147
(58) Field of Search ........................ 702/127; 348/126, 348/91, 135; 382/145, 147, 162, 165, 150, 141; 345/630; 714/4

(56) References Cited

U.S. PATENT DOCUMENTS 5,483,603 A * 1/1996 Luke et al. ................. 382/147
5,638,499 A * 6/1997 O'Connor et al. .......... 345/630

OTHER PUBLICATIONS

DeMarsh, "Colorimetric Standards in U.S. Color Television," A report to the Subcommittee on Systems Colorimetry of the SMPTE Television Committee J. Society of Motion Picture and Television Engineers, vol. 83, No. 1, pp 1–5 (1974).

* cited by examiner

Primary Examiner—John Barlow
Assistant Examiner—Sun Xiuqin
(74) Attorney, Agent, or Firm—Townsend and Townsend and Crew LLP; Kenneth R. Allen

(57) ABSTRACT

A color optical inspection system extracts only such luma and chroma spatial features as are necessary for detection of defects related to the physical characteristics of devices populating the surface of a board. During the training phase, the features of each device present on each of a number of golden boards is extracted and compared against a set of established criteria, thereby to select one or more spatial features to be extracted for the associated devices during the inspection phase. A match region whose boundaries are defined by the selected features of the devices on the golden boards is established during the training phase. During the inspection phase, the selected features of each associated device are extracted to determine whether they fall inside the match region. If the extracted features falls outside the corresponding match region, then a defect is reported.

57 Claims, 4 Drawing Sheets

COLOR OPTICAL INSPECTION SYSTEM

CROSS-REFERENCE TO RELATED APPLICATION

The present application claims benefit of the filing date of the provisional application serial No. 60/214,466, entitled "Substrate Inspection System" and filed on Jun. 27, 2000, the entire content of which is incorporated herein by reference.

BACKGROUND OF THE INVENTION

The present invention relates to optical inspection systems of electronic assemblies, and more particularly to color optical inspection of devices present on a printed circuit board.

Printed circuit boards (PCB) are typically populated by a number of discrete electrical devices, such as capacitors, inductors, resistors, as well as Integrated Circuits (ICs), all of which are mounted on the PCB surface. The process of assembling devices on a PCB is typically highly automated. In most conventional PCB assembly systems, a computer aided design (CAD) tool is used to identify the mounting position of each device, as well as the connections between each device's pins and the electrically conductive traces present on the PCB surface. However, even though highly automated, PCB assembly processes are prone to defects. Therefore, following assembly, each PCB is preferably inspected for possible defects.

Defects on a PCB may be of different types and arise from varying sources. For example, PCB defects may be caused by missing devices, misaligned or tilted devices, wrong devices, soldering defects, etc.

PCB defect detection systems are generally based on one of the following three broad categories: x-ray, laser scanning and visual (optical) inspection systems.

In an x-ray inspection system, an x-ray beam is passed through a PCB assembly to generate an x-ray image of the PCB assembly. X-ray inspection systems, while very accurate in detecting certain classes of defects, such as solder-related defects, are not suited for detecting defects caused by certain other classes of defects, such as those arising from, e.g., misplaced devices.

Laser scanning inspection systems scan a laser beam across the surface of a PCB assembly to form a three-dimensional image of the PCB assembly. Thereafter, the three-dimensional image of the PCB assembly is compared with that of a known defect-free PCB assembly to identify certain types of possible defects. Like x-ray inspection systems, laser scanning inspection systems also have a limited defect detection capability. For example, a laser scanning inspection system typically cannot identify a defect caused by a mounted resistor which has a wrong resistance value.

Optical inspection systems can capture an image of a PCB assembly via a camera system and compare the captured image with that of a defect-free PCB assembly in order to detect possible defects. Both monochrome as well as color optical inspection systems are available and used.

Monochrome optical inspection systems can only form gray scale images of a PCB assembly. Therefore, such systems cannot capture and process any information related to color features of a PCB device. For example, monochrome optical inspection systems cannot identify the value of a discrete resistor's resistance—which is typically coded by the color of rings present on the outer surface of the resistor. Similarly, monochrome optical inspection systems are unable to match the color of a device to that of a reference device to verify, for example, that the device is mounted in its designated PCB position.

In order to rectify the problems stemming from the color-blindness of the prior art monochrome optical inspection systems, color optical inspection systems have been developed. Prior art color optical inspection systems, however, are either costly or slow when required to operate reliably, that is to operate with a certain defect detection accuracy.

Some prior art color optical inspection systems contain parallel image processing capability to thereby speed up their inspection rate. They are typically costly to purchase and maintain. Other prior art color inspection systems contain a single image processing stage and are thus less expensive than multi-stage parallel image processing systems. However, depending on the required level of defect detection accuracy, such systems require a number of execution cycles to form and compare images and thus have a relatively slower throughput.

BRIEF SUMMARY OF THE INVENTION

According to the invention, a color optical inspection system is provided which extracts only such luma and chroma spatial features as are necessary for detection of defects related to physical characteristics of the devices populating the surface of a board, such as a printed circuit board (PCB). The color optical inspection system carries out defect detection in two phases, a training phase followed by an inspection phase.

During the training phase, the color optical inspection system, with the help of an operator, extracts spatial features of each device present on each of a number of golden boards—which are known to contain no defects. The extracted spatial features of each device on the golden boards are compared against a set of established criteria to identify and select one or more spatial features to be extracted for the associated devices (associated devices are devices appearing on the same physical locations on all the PCBs, golden or otherwise) during the inspection phase. Furthermore, for similarly located devices on the golden boards, a match region whose boundaries are defined by the selected spatial feature(s) of that device is established.

During the inspection phase, the selected spatial feature(s) of each device on the PCB is extracted to determine whether it falls inside a corresponding match region. If the extracted feature(s) falls inside the corresponding match region, no defect is reported, otherwise color optical inspection system 10 reports both the presence as well as the position of the defect on the PCB undergoing inspection.

In a specific embodiment, the color inspection system of the present invention includes an image acquisition system and an image feature extraction system. The image acquisition system includes, among other components, a Bayer color filter, a charge coupled device (CCD) imager, an interpolator and a gamma corrector 28. The image feature extraction system includes a color component converter and a number of spatial feature extractors.

In operation, light received from a device passes through a Bayer color filter before reaching an M×N array of CCD light sensitive pixels. The Bayer color filter contains an M×N array of red, green and blue color filters so positioned as to match the corresponding positions of the M×N array of pixels of the CCD imager, which in response generates an M×N array of digitized signals for each of the color components red, green and blue. The signals generated by the CCD imager are applied to an interpolator which performs a bilinear spatial interpolation on the applied signals and which are subsequently corrected for the gamma factor by a gamma corrector.

The gamma-corrected signals, each of which includes an array of M×N signals, are applied to a color component converter which reduces the degree of correlation of the signals applied thereto, thereby to generate a luma component and two orthogonal chroma components of the viewed device.

The luma and chroma color component signals generated by the color component converter are subsequently applied to respective spatial feature extractors which respectively extract spatial features associated with the device in view.

Depending on the values of the three spatial features of each device on the golden boards, one, two or all three spatial features of the associated device may be extracted during the inspection phase. If, during the training phase of a device, only the first spatial feature is selected for defect detection, then during the subsequent inspection phase, the second and third spatial features of the associated device are not extracted.

If, for example, an integrated circuit (IC) is in view, because only black (or gray) and white colors are typically present on its surface, the second and third spatial features of the IC—which represent its chroma components—are not extracted during the inspection phase, in accordance with the selection made during the training phase. To determine the presence or absence of a defect due to the IC, the extracted spatial feature of the IC—representative of its luma component—is mapped onto a one-dimensional region which contains a match region defined by the respective luma component of the associated device as extracted during the training phase. If the extracted spatial feature falls outside the match region, a defect is reported.

If, for example, a capacitor is in view, because of its color uniformity, only the spatial features representative of the luma and one of the chroma color components are extracted during the inspection phase, in accordance with the selection made during the training phase. To determine the presence or absence of a defect related to the capacitor, the extracted spatial features are mapped onto a two-dimensional region which contains a match region defined by the respective luma component and the single chroma component of the associated device as extracted during the training phase. If the extracted spatial features fall outside the match region, a defect is reported.

If, for example, a resistor is in view, because of the presence of multiple colors on its surface, all three spatial features are extracted during the inspection phase, in accordance with the selection made during the training phase. To determine the presence or absence of a defect related to the resistor, the extracted spatial features are mapped onto a three-dimensional region which contains a match region defined by the respective luma component and the two chroma components of the associated device as extracted during the training phase. If the extracted spatial features fall outside the match region a defect is reported.

DETAILED DESCRIPTION OF THE INVENTION

Figure 1:
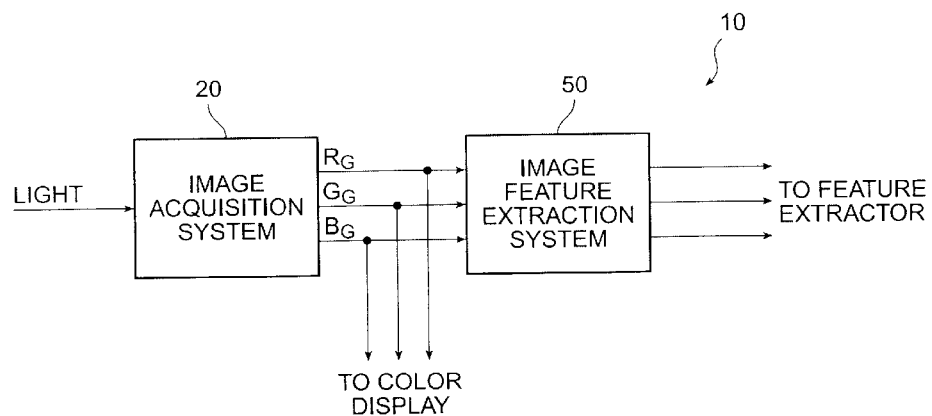
FIG. 1 is a simplified block diagram of a color optical inspection system, in accordance with one embodiment of the present invention.

FIG. 1 is a simplified block diagram of a color optical inspection system 10, in accordance with one embodiment of the present invention. Color optical inspection system 10 includes an image acquisition system 20 and an image feature extraction system 50. To inspect and detect visual defects on a board, such as those visible on a printed circuit board (PCB), one or more luma and/or chroma spatial features of each device on the PCB (not shown) are extracted and subsequently compared with those of an associated device on a reference defect-free board, also referred to as a golden board (not shown). The color optical inspection system carries out defect detection in two phases, a training phase followed by an inspection phase.

During the training phase, the color optical inspection system, with the help of an operator, extracts spatial features of each device present on each of a number of "golden boards," that is, devices which are known to contain no defects. The extracted spatial features of each device on the golden boards are compared against a set of established criteria to identify and select one or more spatial features to be extracted for the associated devices (associated devices are devices appearing on the same physical locations on all the PCBs, golden or otherwise) during the inspection phase. Furthermore, for each similarly located devices on the golden boards, a match region whose boundaries are defined by the selected spatial feature(s) of that device is established.

During the inspection phase, the selected spatial feature(s) of each device on the PCB is extracted to determine whether it falls inside a corresponding match region. If the extracted feature(s) falls inside the corresponding match region, no defect is reported, otherwise color optical inspection system 10 reports both the presence as well as the position of the defect on the PCB undergoing inspection. The various stages of the defect detection performed by the optical color inspection system of the present invention are described below.

Image Acquisition and Image Feature Extraction Systems

Figure 2:
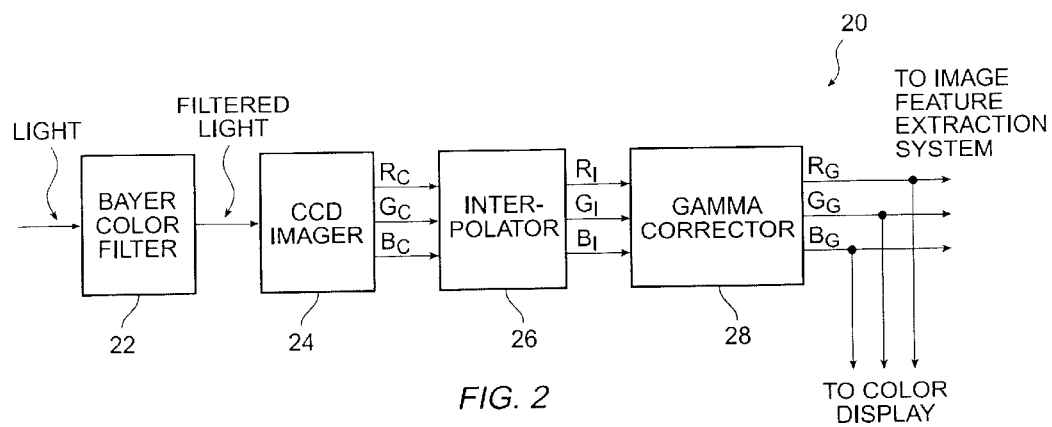
FIG. 2 is a simplified block diagram of an image acquisition system of the color optical inspection system of FIG. 1, in accordance with one embodiment of the present invention.
Figure 3:
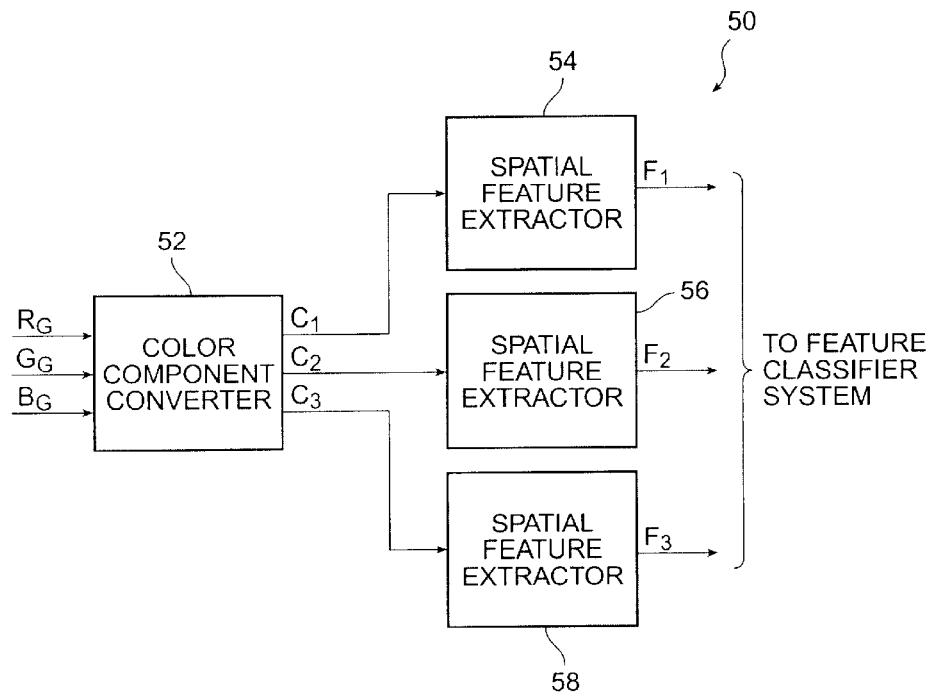
FIG. 3 is a simplified block diagram of an image feature extraction system of the color optical inspection system of FIG. 1, in accordance with one embodiment of the present invention.

FIG. 2 is a simplified block diagram of the various components forming the image acquisition system 20 in accordance with one embodiment of the present invention. Image acquisition system 20 includes, among other components, a Bayer color filter 22, a charge coupled device (CCD) imager 24, an interpolator 26 and a gamma corrector 28. Image acquisition system 20 acquires images of devices present on the golden boards during the training phase as well as those of associated devices present on the PCBs during the inspection phase.

In operation, light received from a device passes through an objective lens (not shown) and is thus focused on Bayer color filter 22 before reaching an M×N array of CCD light sensitive pixels present on the surface of CCD imager 24. Bayer color filter 22, which is known in the prior art, contains an M×N array of red, green and blue color filters so positioned as to match the corresponding positions of the M×N array of pixels of CCD imager 24. The M×N array of red, green and blue color filters of Bayer filter 22 are shown below:

RGRGR . . .
GBGBG . . .
RGRGR
. . .

in which letters R, G and B respectively denote colors red, green and blue.

After passing through Bayer color filter 22, the light received from a device reaches the pixels forming CCD imager 24, which in response generates an M×N array of digitized signals for each of the color components red, green and blue, as known in the prior art. Each of signals $R_C$, $G_C$ and $B_C$ generated by CCD imager 24 includes an array of M×N signals.

Signals $R_C$, $G_C$ and $B_C$ generated by CCD imager 24 are applied to interpolator 26, which linearly interpolates the applied signals to generate signals $R_I$, $G_I$ and $B_I$. Each of signals $R_I$, $G_I$ and $B_I$ also includes an M×N array of signals and each has a value that is linearly proportional to the luminance of the light incident upon the corresponding pixels of CCD imager 24. In a specific embodiment, interpolator 26 performs a bilinear interpolation, as illustrated below.

Consider a 4×4 pixel array surrounding a 2×2 pixel quad, as shown below:

| | | | |
|---|---|---|---|
| P(x − 1, y − 1) | P(x, y − 1) | P(x + 1, y − 1) | P(x + 2, y − 1) |
| P(x − 1, y) | P(x, y) | P(x + 1, y) | P(x + 2, y) |
| P(x − 1, y + 1) | P(x, y + 1) | P(x + 1, y + 1) | P(x + 2, y + 1) |
| P(x − 1, y + 2) | P(x, y + 2) | P(x + 1, y + 2) | p(x + 2, y + 2) |

Assume that (i) pixel P(x, y) (i.e., the pixel with coordinates x and y) corresponds to a red filter pixel R(x, y), (ii) pixel P(x+1, y) corresponds to the green filter pixel G(x+1, y), (iii) pixel P(x, y+1) corresponds to the green filter pixel G(x, y+1), and (iv) pixel P(x+1, y+1) corresponds to the blue filter pixel G(x+1, y+1). The bilinear interpolation of pixel values performed by interpolator 26 is as follows:

R(x, y)=P(x, y)
R(x+1, y)=[P(x, y)+P(x+2, y)]/2
R(x, y+1)=[P(x, y)+P(x, y+2)]/2
R(x+1, y+1)=[P(x, y)+P(x+2, y)+P(x, y+2)+P(x+2, y+2)]/4
G(x, y)=[P(x, y−1)+P(x−1, y)+P(x+1, y)+P(x, y+1)]/4
G(x+1, y)=P(x+1, y)
G(x, y+1)=P(x, y+1)
G(x+1, y+1)=[P(x+1, y)+P(x, y+1)+P(x+2, y+1)+P(x+1, y+2)]/4
B(x, y)=[P(x−1, y−1)+P(x+1, y−1)+P(x−1, y+1)+P(x+1, y+1)]/4
B(x+1, y)=[P(x+1, y−1)+P(x+1, y+1)]/2
B(x, y+1)=[P(x−1, y+1)+P(x+1, y+1)]/2
B(x+1, y+1)=P(x+1, y+1)

When an RGB pixel quad is located at an edge of a pixel array, the interpolations are performed by reflection of adjacent pixels about that edge.

The linearly interpolated signals $R_I$, $G_I$ and $B_I$ are applied to gamma corrector 28 which corrects the applied signals for the gamma factor, thereby generating signals $R_G$, $G_G$ and $B_G$, as known in the prior art and shown below:

$G_G = R_I^{0.45}$
$G_G = G_I^{0.45}$
$B_G = B_I^{0.45}$

Each of gamma-corrected signals $R_G$, $G_G$ and $B_G$ includes an array of M×N gamma-corrected signals and is delivered to a color display monitor (not shown) as well as to image feature extraction system 50, as described below.

Image feature extraction system 50 includes, among other components, a color component converter 52 and three spatial feature extractors 54, 56 and 58. Image feature extraction system 50 receives the gamma-corrected signals $R_G$, $G_G$ and $B_G$ of a device and, depending on the surface characteristics of the device, generates one or more spatial features $F_1$, $F_2$ and $F_3$.

Gamma-corrected signals $R_G$, $G_G$ and $B_G$ generated by gamma corrector 28 may be highly correlated with one another, thereby complicating accurate classification and inspection of the viewed devices. To reduce the degree of such a correlation, gamma-corrected signals $R_G$, $G_G$ and $B_G$ are converted by color component converter 52 to signals representative of a luma component $C_1$ and two orthogonal chroma components $C_2$ and $C_3$ of the viewed device. The conversion by color component converter 52 is carried out in two stages.

First, color component converter transforms color component signals $R_G$, $G_G$ and $B_G$ to color component signals Y, $C_b$, $C_r$, as known in the prior art, using the following linear transformation matrix:

$$\begin{bmatrix} Y \\ C_b \\ C_r \end{bmatrix} = \begin{bmatrix} 0.29900000 & 0.58700000 & 0.11400000 \\ -0.16873600 & -0.33126400 & 0.50000000 \\ 0.50000000 & -0.4186680 & -0.08131200 \end{bmatrix} \begin{bmatrix} R_S \\ G_S \\ B_S \end{bmatrix}$$

It is understood that the Y, $C_b$, $C_r$ color coordinate system is not the same as the YUV color coordinate system employed in the European color television systems. The Y, $C_b$, $C_r$ color coordinate system separates the luma component Y, which is related to intensity of the light received from a device, from the chroma components $C_b$ and $C_r$, which are jointly related to hue and saturation of the light received from the device.

Next, to further simplify the pattern classification of the viewed devices (e.g., by a feature classifier system, not shown) the two chroma signals $C_b$ and $C_r$ are converted to color component signals $C_2$ and $C_3$—which are respectively related to hue and saturation.

Color component signals $C_1$, $C_2$ and $C_3$ are obtained from color component signals Y, $C_b$ and $C_r$ in accordance with the following relationships:

$$C_1 = Y$$

$$C_2 = \arctan\left[\frac{C_r}{C_b}\right]$$

$$C_3 = [C_r^2 + C_b^2]^{1/2}$$

Color component signals $C_1$, $C_2$ and $C_3$ are respectively applied to spatial feature extractors 54, 56 and 58, which respectively generate spatial feature signals $F_1$, $F_2$ and $F_3$. A multitude of spatial features may be extracted from each color component of the light received from a device that may serve as the basis for identifying that device.

Figure 4:
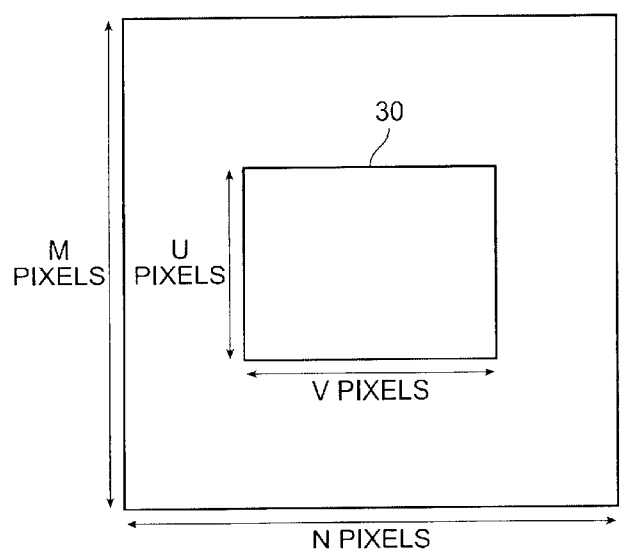
FIG. 4 is a simplified image of a device captured by a subarray of the pixel arrays of the color optical inspection system of FIG. 1.

For each of color component signals $C_1$, $C_2$ and $C_3$, one such spatial feature is obtained by taking the average value (over a device area or a region) of all the signals that, in the aggregate, form that color component signal. For example, as illustrated in FIG. 4, assume that a device image 30 is entirely captured by an U×V array of pixels, which array is a subarray of the M×N array of pixels of color optical inspection system 10. Each signal $C_1$, $C_2$ and $C_3$ corresponding to image 30 includes an array of U×V pixels covering the area of the device. Therefore, for example, spatial feature extractor 56 of the viewed device may be configured to extract spatial feature $F_2$ by computing the average of the U×V pixels included in color component signal $C_2$.

Other methods for extracting spatial features include using template matching, histogram shape or edge gradient density of the color components of the light received from a device. Spatial feature extractors 52, 54 and 56 are further explained below.

Template matching is a technique for detecting objects within a search field. In accordance with the template matching technique, an image of a template object is compared to that of an unknown object in a search field to compute a template match score. If the template match score is greater than a predefined value, then the unknown object is deemed to match the template object. For a more detailed description of the template matching technique, see, for example, "Digital Image Processing", Second Edition, by William K. Pratt, published by John Wiley & Sons, Inc. 1991, pages 651–673, the contents of which pages are incorporated herein by references in their entirety.

The statistical data gathered on signals $F_1$, $F_2$ and $F_3$ during the data collection of training phase are used to define device match regions for identification of matches during the inspection phase. In one embodiment, the mean values of signals $F_1$, $F_2$ and $F_3$ and the cross-correlation values of signals $F_1$, $F_2$ and $F_3$ may be used to define the match regions, as described further below.

Training Phase: Data Collection

During the training phase, color component signals $C_1$, $C_2$ and $C_3$ of the light received from each device present on each of a number of golden boards, for example 20 golden boards, are generated by color optical inspection system 10, as described above. Next, spatial feature extractors 52, 54 and 56 respectively extract corresponding spatial feature signals $F_1$, $F_2$ and $F_3$ of all such devices (i.e., computed) as described below.

Spatial feature signal $F_1$ of devices appearing on the same positions of the golden boards is computed as follows. Color optical inspection system 10 generates the color component signals $C_1$ of the lights received from all devices occupying the same positions on the various golden boards. Thereafter, a module computes the template match score of the color component signal $C_1$ of all such similarly positioned devices on the golden boards. In accordance with one embodiment, signal $F_1$ is the template match score between signals $C_1$, each of which includes an array of U×V pixels covering the device's image (see FIG. 4). In accordance with one embodiment, the template match score is the peak value of the cross-correlation values between the pixels of the template and those within the search field.

Spatial feature signal $F_2$ of devices appearing on the same positions of the golden boards is computed as follows. Color optical inspection system 10 generates the color component signals $C_2$ of the lights received from all devices occupying the same positions on the various golden boards. Thereafter, a module computes the average of all such color component signals $C_2$. Signal $F_2$ is the average value of signals $C_2$ each of which includes an array of U×V pixels covering the device's image.

Spatial feature signal $F_3$ of devices appearing on the same positions of the golden boards is computed as follows. Color optical inspection system 10 generates the color component signals $C_3$ of the light received from all devices occupying the same positions on the various golden boards. Thereafter, a module computes the average of all such color component signals $C_3$. Signal $F_3$ is the average value of signals $C_3$ each of which includes an array of U×V pixels covering the device's image.

Training Phase: Data Analysis

Spatial feature signals $F_2$ and $F_3$ computed for each device on the golden boards are further analyzed by a module to determine whether such spatial signals are to be computed for the associated devices on the PCBs.

If, during the training phase, the value of each of signals $F_2$ and $F_3$ is determined to be below a certain threshold value for a device, then, during the inspection phase, only spatial feature $F_1$ of the associated device is extracted.

For example, assume that during the training phase an integrated circuit (IC) is in view. Assume that the IC is conventional and therefore has a black or gray package on the top surface upon which a white alphanumeric number designating its model number is printed. Because only black (or gray) and white colors are present on the surface of such an IC, the signals $F_2$ and $F_3$ of such an IC will have relatively small values. Accordingly, during the inspection phase of a PCB, when an associated IC is in view, optical color inspection system 10, advantageously and in accordance with the present invention, extracts only spatial signal $F_1$. Consequently, optical color inspection system 10, by not computing spatial features signals $F_2$ and $F_3$ of such an IC during the inspection phase, carries out fewer computations than prior art optical inspection systems.

Figure 5A:
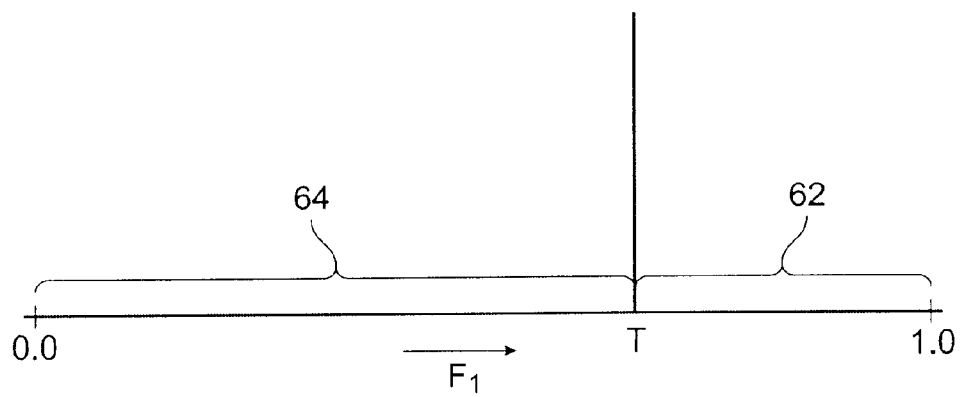
FIG. 5A illustrates a one-dimensional device match region, in accordance with one embodiment of the present invention.

If during the training phase it is determined that only signal $F_1$ of a device is required for identifying matches (i.e., for detecting defects), a threshold value defined by signal $F_1$ of the device, as computed during the training phase, is established for determination of subsequent matches during the inspection phase. FIG. 5A illustrates a threshold value T separating matching region 62 from non-matching region 64 for devices for which only spatial feature signal $F_1$ is extracted during the inspection phase (e.g., an IC). In accordance with FIG. 5A, an associated device with an extracted $F_1$ value greater than T is considered a matching device (i.e., a defect-free device) while an associated device with an extracted $F_1$ value smaller than T is considered a non-matching device (i.e., a defective device).

If during the training phase, the value of either signal $F_2$ and/or $F_3$ is determined to be above a certain threshold value for a device, then, during the inspection phase either (i) spatial feature signals $F_1$ and $F_2$ or (ii) spatial feature signals $F_1$ and $F_3$, or (iii) spatial feature signals $F_1$, $F_2$ and $F_3$ of the associated device are extracted.

For example, assume that during the training phase a discrete capacitor is in view. Most conventional capacitors have a beige or light brown color with no identification number. Further, assume that during the training phase spatial feature signals $F_1$ and $F_2$ of the capacitor are determined to have numerically significant values (i.e., each is greater than a predefined value) while spatial feature signals $F_3$ of the capacitor is found to have a numerically insignificant value. Accordingly, during the inspection phase of a PCB when an associated capacitor is in view, optical color inspection system 10, advantageously and in accordance with the present invention, only extracts spatial feature signals $F_1$ and $F_2$. Consequently, optical color inspection system 10 by not computing spatial feature signal $F_3$ of such a capacitor during the inspection phase, carries out fewer computations than prior art optical inspection systems.

Figure 5B:
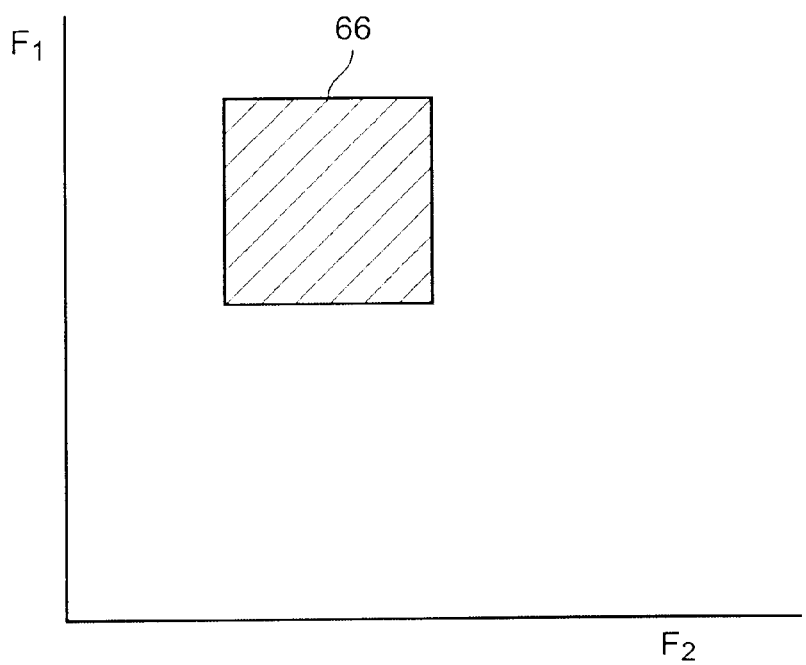
FIGS. 5B and 5C each illustrate a two-dimensional device match region, in accordance with one embodiment of the present invention.

If during the training phase it is determined that only signals $F_1$ and $F_2$ of a device are required for identifying matches, a region whose boundaries are defined by the mean and cross-correlation of signals $F_1$ and $F_2$ of the device—as computed during the training phase—is established for determination of subsequent matches during the inspection phase. FIG. 5B illustrates a matching region 66 whose boundaries are defined by the mean and cross-correlation of signals $F_1$ and $F_2$, as extracted during the training phase. In FIG. 5B, an associated device with a combined extracted $F_1$ and $F_2$ value falling inside region 66 is considered a matching device, while an associated device with a combined extracted $F_1$ and $F_2$ value falling outside region 66 is considered a non-matching device.

Figure 5C:
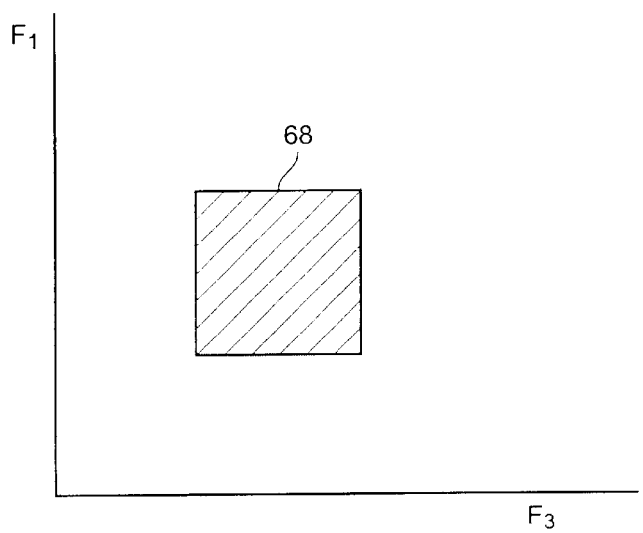

If during the training phase of a device it is determined that spatial feature signals $F_1$, $F_3$ have numerically significant values while spatial feature signals $F_2$ is found to have numerically insignificant value, then, during the subsequent inspection phase when an associated device is in view, only spatial feature signals $F_1$ and $F_3$ are extracted. Accordingly, a region whose boundaries are defined by the mean and cross-correlation of signals $F_1$ and $F_3$—as computed during the training phase—is established for determination of subsequent matches during the inspection phase. FIG. 5C shows a matching region 68 whose boundaries are defined by the mean and cross-correlation of signals $F_1$ and $F_3$, as extracted during the training phase. In FIG. 5C, an associated device with a combined extracted spatial feature signal $F_1$ and $F_3$ value falling inside region 68 is considered a matching device, while an associated device with a combined extracted $F_1$ and $F_3$ value falling outside region 68 is considered a non-matching device.

A device may exhibit surface characteristics, e.g. color and size, that necessities the determination of all three spatial features $F_1$, $F_2$ and $F_3$. For example, a discrete resistor has a resistance value that is coded in the color of the rings present on its surface. Accordingly, all three signals $F_1$, $F_3$ and $F_3$ may be required to correctly identify and inspect such a resistor, as described below.

Assume that during the training phase a discrete resistor is in view. Further, assume that during the training phase, due to its outer surface characteristics, spatial feature signals $F_1$, $F_2$ and $F_3$ of the resistor are determined to have numerically significant values. Accordingly, during the inspection phase when an associated resistor is in view, all three spatial feature signals $F_1$, $F_2$ and $F_3$ are extracted. Accordingly, optical color inspection system 10, advantageously and in accordance with the present invention, extracts all three spatial feature signals $F_1$, $F_2$ and $F_3$ only when all three spatial feature signals $F_1$, $F_2$ and $F_3$ are required for matching.

Figure 5D:
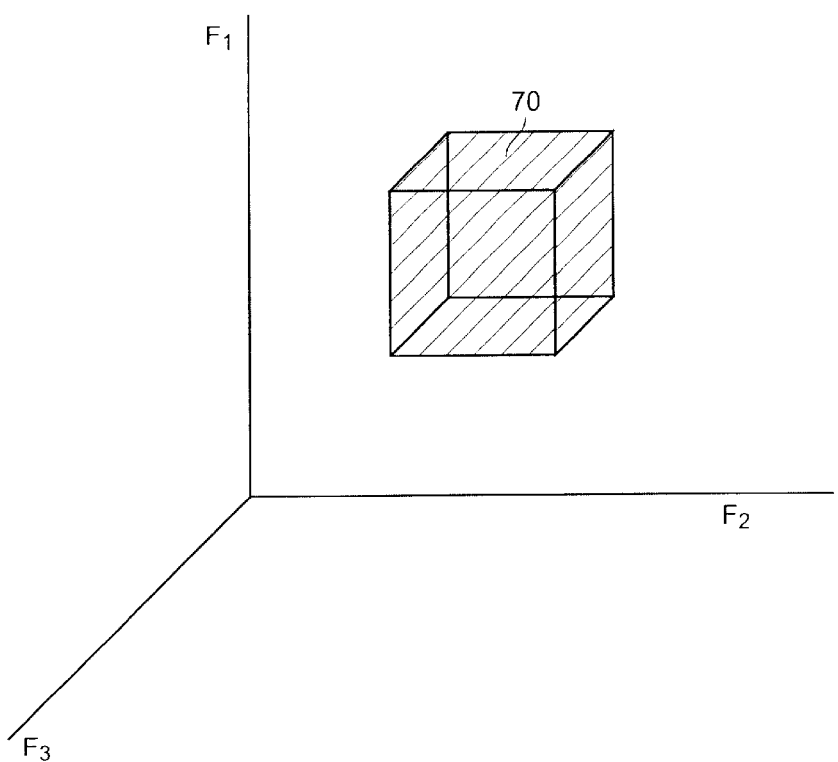
FIG. 5D illustrates a three-dimensional device match region, in accordance with one embodiment of the present invention.

If during the training phase it is determined that all three spatial feature signals $F_1$, $F_2$ and $F_3$ of a device are required for identifying matches, a region whose boundaries are defined by the cross-correlation of signals $F_1$, $F_2$ and $F_3$ of that device, as computed during the training phase, is established for determination of subsequent matches during the inspection phase. FIG. 5D shows a matching region 70 whose boundaries are defined by the mean and cross-correlation of signals $F_1$, $F_2$ and $F_3$, as extracted during the training phase. In FIG. 5D, an associated device with a combined extracted $F_1$, $F_2$ and $F_3$ value falling inside region 70 is considered a matching device, while an associated device with extracted $F_1$, $F_2$ and $F_3$ values falling outside region 70 is considered a non-matching device.

Inspection Phase

After each device on the golden boards has been characterized during the training phase by the color optical inspection system 10 and a matching region for each such device on the golden boards has been defined, the inspection phase begins.

During the inspection phase, each device on the PCBs is brought under view to determine its coordinates. Thereafter, color optical inspection system 10 identifies the associated device on the golden boards, which in turn identifies which of the spatial features are to be extracted for that device.

If, for example, an IC is in view, only spatial feature signal $F_1$ is extracted. For each device in view, spatial feature signal $F_1$ is extracted by computing the template match score between the color component signal $C_1$ of that device and the color component signals $C_1$ of the associated devices. To determine whether the IC is a matching IC, the extracted $F_1$ value of the device is mapped onto the one-dimensional match region defined during the training phase (see FIG. 5A). If the extracted $F_1$ of the IC falls inside, for example, match region 62, the IC is considered a matching IC. If the extracted $F_1$ of the IC falls outside match region 62, the IC is considered a non-matching IC, thereby causing color optical inspection system 10 to report the presence of a defect at the location of the IC on the PCB.

If, for example, a capacitor is in view, only spatial feature signals $F_1$ and $F_2$ are extracted. For each device in view, spatial feature signal $F_2$ is extracted by computing the average of all the signals (e.g. U×V signals), which in the aggregate form the color component signal $C_2$ of that device. To determine whether the capacitor is a matching capacitor, the two-dimensional coordinates of extracted signals $F_1$ and $F_2$ of the capacitor is computed. Next, the coordinates are compared against the corresponding match region defined during the training phase (see FIG. 5B). If the point defined by the coordinates of the extracted $F_1$ and $F_2$ of the capacitor falls inside, for example, match region 66, the capacitor is considered a matching capacitor. If the point defined by the coordinates of the extracted $F_1$ and $F_2$ of the capacitor falls outside match region 66, the capacitor is considered a non-matching capacitor, thereby causing color optical inspection system 10 to report the presence of a defect at the location of the capacitor on the PCB.

If, for example, a resistor is in view, all three spatial feature signals $F_1$, $F_2$ and $F_3$ are extracted. For each device in view, spatial feature signal $F_3$ is extracted by computing the average of all the signals, which in the aggregate form the color component signal $C_3$ of that device. To determine whether the resistor is a matching resistor, the three-dimensional coordinates of the extracted signals $F_1$, $F_2$ and $F_3$ of the resistor is computed and mapped onto the three-dimensional region which includes the corresponding match region defined during the training phase (see FIG. 5D). If the point defined by the coordinates of the extracted signals $F_1$, $F_2$ and $F_3$ of the resistor fall inside, for example, match region 70, the resistor is considered a matching resistor. If the point defined by coordinates of the extracted $F_1$, $F_2$ and $F_3$ of the resistor falls outside match region 70, the resistor is considered a non-matching resistor, thereby causing color optical inspection system 10 to report the presence of a defect at the location of the resistor on the PCB.

The specific embodiments of the present invention described above are illustrative and not limitative and various modifications, alterations, alternative constructions, and equivalents thereof are also encompassed within the scope of the invention.

The invention is not limited by the manner which various components of the lights received from the PCB devices are acquired and extracted. The invention is not limited by the type of image sensor, Interpolator, gamma-corrector, color component converter and spatial feature extractor that form the color inspection system of the present invention. For example, it is understood that spatial features include any measurable features whether one dimensional spatial features (points) or multidimensional spatial features. The invention is not limited by the type of statistical analysis, such as mean, or cross-correlation, that is used for feature classification and defect detection.

The invention is not limited by the manner with which the match regions are defined. For example, any number of conventional statistical analysis and techniques, cross-correlation or otherwise, may be performed to compute a joint probability distribution used to define a two-dimensional or a three-dimensional match region.

The invention is not limited by the number of spatial features extracted by each of the three spatial feature extractors of the optical color inspection of the present invention. For example, each spatial feature extractor may extract two or more spatial features of a light received from a viewed device.

Additions, subtractions, deletions, and other modifications and changes to the present invention may be made thereto without departing from the scope of the present invention as is set forth in the appended claims.

What is claimed is:

1. A method for color inspection of a device present on a surface, the method comprising:
   computing measurable feature data related to first, second and third components of light in a first color space and received from at least one associated device present on a second surface;
   comparing values of the second and third components of the light in the first color since and received from the at least one associated device with first and second predefined values;
   computing only data related to the first component of light in the first color space and received from the device if the values of the second and third components of the light in the first color space and received from the at least one associated device are respectively smaller than first and second predefined values; and
   reporting a defect if the value of the first component of the light in the first color space and received from the device is smaller than a threshold value defined by the value of the first component of the light in the first color space and received from the at least one associated device.

2. The method of claim 1 wherein the measurable features are spatial features.

3. The method of claim 1 wherein the measurable features are point features.

4. A method for color inspection of a device present on a surface, the method comprising:
   computing measurable feature data related to first, second and third components of light in a first color space and received from at least one associated device present on a second surface;
   computing only data related to the first component of light in the first color space and received from the device if the values of the second and third components of the light in the first color since and received from the at least one associated device are respectively smaller than first and second predefined values;
   reporting a defect if the value of the first component of the light in the first color apace and received from the device is smaller than a threshold value defined by the value of the first component of the light in the first color space and receive from the at least one associated device;
   computing measurable feature data related to the second component of the light in the first color space and received from the device only if the value of the second component of the light in the first color space and received from the at least one associated device is greater than the first predefined value; and
   reporting a defect if the values of the first and second components of the light in the first color space and received from the device are not within a two-dimensional region defined by the values of the first and second components of the light in the first color space and received from the at least one associated device.

5. The method of claim 4 further comprising:
   computing measurable feature data related to the third component of the light in the first color space and received from the device only if to value of the third component of the light in the first color space and received from the at least one associated device is greater than the second predefined value; and
   reporting a defect if the values of the first, second and third components light in the first color space and received from the device are not within a three-dimensional region defined by thin values of the first, second and third components of the light in the first color space and received from the at least one associated device.

6. The method of claim 5 wherein said first component of the light in the first color space is related to the brightness intensity component of the received light.

7. The method of claim 6 wherein said second component of the light in the first color space is related to the hue component of to received light.

8. The method of claim 7 wherein said third component of to light in the first color space is related to the saturation component of the received light.

9. The method of claim 8 wherein the at least one associated device further comprises at least first and second associated devices each disposed on a different surface, and wherein the intensity component of the lights received from the at least first and second associated devices is related to template match score of luma components of the lights received from the at least first and second associated devices, wherein the luma components of the lights define a dimension in a second color space.

10. The method of claim 9 wherein the hue component of the lights received from the at least first and second associated devices is related to respective spatial average of first chroma components of the lights received from the at least first and second associated devices, wherein the first chroma components of the lights define a second dimension in the second color space.

11. The method of claim 10 wherein the saturation component of the lights received from the at least first and second associated device, is related to respective spatial avenge of second chroma components of the lights received from the at least first and second associated devices, wherein the first chroma components of the lights defines a third dimension in the second color space.

12. The method of claim 11 wherein the intensity, component of the light received from to device is related to template match score of luma components of the lights received from each of the device and the tint and second associated devices.

13. The method of claim 12 wherein the hue component of the light received from the device is related to avenge of the first chroma components of the light received from the device.

14. The method of claim 13 wherein to saturation component of the light received from the device is related to average of the second chroma components of the light received from to device.

15. The method of claim 14 wherein the luma component in the second color space of to lights received from each of the at least first and second associated devices is equal to respective luma component Y in a third color space of to lights received from to at least first and second associated devices.

16. The method of claim 15 wherein the first chroma component in the second color space of the lights received from each of the at least first and second associated devices is related to respective chroma components $C_b$ and $C_r$ in the third color space of the lights received from each of the at least first and second associated devices.

17. The method of claim 16 therein the first chroma component in the second color space of the light received from each of to at least first and second associated devices is equal to the respective arrangement of to ratio of the chroma components $C_b$ and $C_r$ in the third color space of the lights received from each of the at least first and second associated devices.

18. The method of claim 16 wherein the second chroma component into second color space of the lights received from each of to at least first and second associated devices is related to the respective chroma components $C_b$ and $C_r$ in the third color space of each of the lights received from each of the at least first and second associated devices.

19. The method of claim 18 wherein the second chroma component in to second color space of the lights received from each of the at lent first and second associated devices is equal to the respective square root of the sum of squares of the chroma color components $C_b$ and $C_r$ in the third color space of the lights received from each of the at least first and second associated devices.

20. The method of claim 18 wherein the luma component in the second color space of the light received from the device is related to luma component Y in the third color space of the light received from device.

21. The method of claim 20 wherein the first chrome component in to second color space of the light received from to device is related to the chrome components $C_b$ and $C_r$ in the third color space of the light received from device.

22. The method of claim 21 wherein the first chroma component in to second color space of to light received from the device is equal to the arctangent of the ratio of the chrome color components $C_{b\ and\ C_r}$ in the third color space of the light received from the device.

23. The method of claim 21 wherein the second chroma component in the second color space of the light received from the device is related to the chroma components $C_b$ and $C_r$ in the third color space of the light received from the device.

24. The method of claim 23 wherein to second chrome component in the second color space of the light received front the device is equal to the square root of the sum of squares of the chrome color components $C_b$ and $C_r$ in the third color space of the light received from the device.

25. The method of claim 24 wherein the Y, $C_b$ and $C_r$ components in the third color space of the lights received from the device and from each of the at least first and second associated devices are related to respective gamma-corrected red, green and blue components of the lights received therefrom.

26. The method of claim 25 wherein the gamma-corrected rod, green and blue components of to lights received from the device and from each of the at least first and second associated devices are bilinearly interpolated from their respective red, green and blue components of the lights generated by an image sensor.

27. The method of claim 26 wherein the lights received from the device and from each of the at least first and second associated devices are filtered by a Bayer color filter before being received by the image sensor.

28. The method of claim 2 wherein to measurable features are spatial features.

29. The method of claim 2 wherein the measurable features an point features.

30. An apparatus for color inspection of a device present on a surface, the apparatus comprising:

measurable feature extractor operative to extract first, second and third components of light in a first color space and received from at least one associated device;

control module operative to compare values of the second and third components of the light in the first color space and received from the at least one associated device with first and second predefined values and to instruct the feature extractor to extract only a first component in the first color space of light received from the device if the values of the second and third components of the light in the first color space and received from the at least one associated device are smaller than respective first and second predefined values; and reporting module operative to report a defect if to value of to first component of the light in the first color space and received from the device is smaller than a threshold value defined by the value of the first component of the light in the first color space and received from the at least one associated device.

31. The apparatus of claim 30 wherein the measurable feature extractor is operative to measure spatial features.

32. The apparatus of claim 30 wherein the measurable feature extractor is operative to measure point features.

33. An apparatus for color inspection of a device present on a surface, the measurable feature extractor operative to extract first, second and third components of light in a first color space and received from at least one associated device;

control module operative to instinct the feature extractor to extract only a first component in the first color space of light received from the device if the values of the second and third components of the light in to first color space and received from to at least one associated device are smaller than respective first and second predefined values; and reporting module operative to report a defect if the value of the first component of the light in the first color space and received from to device is smaller than a threshold value defined by the value of the first component of the light in the first color space and received from the at least one associated device wherein the control module is operative to instruct the feature extractor to extract a second component in the first color space of the light received from the device only if the value of the second component of the light in the first color space and received from the at least one associated device is greater than the first predefined value, wherein the reporting module is operative to report a defect if the values of the first and second components of the light in the first color space and received from the device is not within a two-dimensional region defined by the values of the first and second components of the light in to first color space and received from the at least one associated device.

34. The apparatus of claim 33 wherein the control module is operative to instruct the feature extractor to extract a third component of the light in the first color space and received from the device only if the value of the third component of light in the first color space and received from to at least one associated device is greater tan the second predefined value, wherein the reporting module is operative to report a defect if the values of the first, second and third components of light in the first color space and received from the device is not within a three-dimensional region defined by the values of the first, second and third components of the light in the first color space and received from the at least one associated device.

35. The apparatus of claim 34 wherein said first component of the light in the first color space is related to the intensity of the received light.

36. The apparatus of claim 35 wherein said second component of the light in the first color space is related to the hue component of the received light.

37. The apparatus of claim 36 wherein said third component of the light in the first color space is related to the saturation component of the received light.

38. The apparatus of claim 37 wherein the at least one associated device further comprises at least first and second associated devices each disposed on associated surface, the apparatus further comprising a first module operative to compute a template match score of luma components in a second color space of the lights received from the at least first and second associated devices, said template match score being related to the intensity component in the tint color space of the lights received from each of to at least first and second associated devices.

39. The apparatus of claim 38 further comprising a second module operative to compute an average of first chroma components in the second color space of the lights received from each of the at least first and second associated devices, said average of the first chroma components being related to the hue components in the first color space of the lights received from cinch of the at least first and second associated devices.

40. The apparatus of claim 38, further comprising a third module operative to compute an average of second chroma components in the second color space of the lights received from each of the at least first and second associated devices, said average of the second chroma components being related to the saturation components in to first color space of the lights received from each of the at least first and second associated devices.

41. The apparatus of claim 40 wherein said first module is operative to compute a template match score of luma components in the second color space of the lights received from the device and from the at least first and second associated devices, said template match score being related to the brightness intensity component in the first color space of the light received from the device.

42. The apparatus of claim 41 wherein said second module is operative to compute an average of first chroma components in the second color space of the lights received from the device and from each of the at least first and second associated devices, said average being related to the hue component in the first color space of the light received from the device.

43. The apparatus of claim 42 wherein said third module is operative to compute an average of second chrome components in the second color space of the lights received from the device and from each of the at least first and second associated devices, said average being related to the saturation component in the first color space of the light received from the device.

44. The apparatus of claim 43 further comprising a color component converter operative to convert a luma component Y in a third color space of the lights received from each of the at least first and second associated devices to the luma component in the second color space of the lights received from each of the first and second associated devices.

45. The apparatus of claim 44 wherein the color component converter is operative to convert chroma components $C_b$ and $C_r$ in the third color space of the lights received from each of the at least first and second associated devices to the first chroma component in the second color space of the lights received from each of the at least first and second associated devices.

46. The apparatus of claim 45 wherein the color component converter is operative to convert chrome components $C_b$ and $C_r$ in the third color space of the lights received from each of the at least first and second associated devices to the second chrome component in the second color space of the lights received from each of the at least first and second associated devices.

47. The apparatus of claim 46 wherein the color component converter is operative to compute an square root of the sum of squares of chroma color components $C_b$ and $C_r$ in the third color space of the lights received from each of the at least first and second associated devices, wherein said square root is related to the second chroma components in the second color space of the lights received from to at least first and second associated devices.

48. The apparatus of claim 47 wherein the color component converter is operative to convert the luma color component Y in the third color space of the light received from the device to the luma component in the second color space of the light received from the device.

49. The apparatus of claim 48 wherein the color component converter is operative to convert the chroma components $C_b$ and $C_r$ in to third color space of the light received from the device to the first chroma component in the second color space of the light received from the device.

50. The apparatus of claim 49 wherein the color component converter is operative to compute an arctangent of to ratio of the drama components $C_b$ and $C_r$ in to third color space of the light received from the device, wherein said arctangent is related to the first chroma component in the second color space of the light received from the device.

51. The apparatus of claim 49 wherein the color component converter is operative to convert the chroma components $C_b$ and $C_r$ in the third color space of to light received from the device to the second chroma component in the second color space of the light received from the device.

52. The apparatus of claim 51 wherein the color component converter is operative to compute a square root of the sum of squares of chroma components $C_b$ and $C_r$ in the third color apace of the light received from the device, wherein said square root is related to the second chroma component in the second color space of the light received from to device.

53. The apparatus of claim 51 wherein the color component converter is operative to receive gamma-corrected rod, green and blue color components and to generate, in response, luma, first chroma and second chroma components in the second color space.

54. The apparatus of claim 53 further comprising:

Bayer color filter;

image sensor coupled to the Bayer color filter to receive the filtered tight therefrom and to generate, in response, red, green and blue color components;

interpolator operative to receive to red, green and blue color components generated byte image sensor and to generate, in response, linearly interpolated red, green and blue color components; and a gamma corrector operative to receive the linearly interpolated red, green and blue color components and to generate, in response, gamma-corrected red, green and blue color components.

55. The apparatus of claim 44 wherein the color component converter is operative to compute an arctangent of the ratio of the chroma color components $C_b$ and $C_r$ in the third color space of the lights received from each of the at least first and second associated devices, wherein said arctangent is related to the first chrome components in the second color space of the lights received from each of the at least first and second associated devices.

56. The apparatus of claim 33 wherein the measurable feature extractor is operative to measure spatial features.

57. The apparatus of claim 33 wherein the measurable feature extractor is operative to measure point features.

* * * * *